United States Patent [19]

Schorr et al.

[11] 4,018,933
[45] Apr. 19, 1977

[54] ACYLAMINOPENICILLANIC ACIDS AND PROCESS FOR PREPARING THEM

[75] Inventors: Manfred Schorr, Frankfurt am Main; Elmar Schrinner, Wiesbaden; Wilfried Schmitt, Kelkheim, Taunus, all of Germany

[73] Assignee: Hoechst Aktiengesellschaft, Frankfurt am Main, Germany

[22] Filed: Dec. 11, 1975

[21] Appl. No.: 639,807

[30] Foreign Application Priority Data

Dec. 13, 1974 Germany .................... 2458973

[52] U.S. Cl. .................... 424/271; 260/239.1
[51] Int. Cl.² ............ C07D 499/68; C07D 499/70; A61K 31/43
[58] Field of Search ............... 260/239.1; 424/271

[56] References Cited
UNITED STATES PATENTS

| | | | |
|---|---|---|---|
| 3,749,711 | 7/1973 | Schorr et al. | 260/239.1 |
| 3,870,709 | 3/1975 | Hamanaka | 260/239.1 |
| 3,935,189 | 1/1976 | Ferres et al. | 260/239.1 |

*Primary Examiner*—Gerald A. Schwartz
*Attorney, Agent, or Firm*—Curtis, Morris & Safford

[57] ABSTRACT

Acylaminopenicillanic acids of the general formula

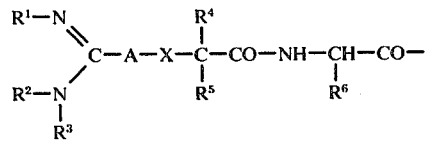

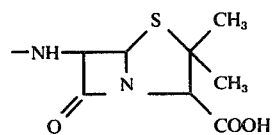

in which $R^1$, $R^2$ and $R^3$ represent hydrogen or lower alkyl which may be substituted, and in which the radicals $R^1$ and $R^2$ or $R^2$ and $R^3$ may form together an alkylene radical which may be substituted, $R^4$ and $R^5$ represent hydrogen or lower alkyl, $R^6$ represents phenyl which may be substituted, a monocyclic aromatic heterocycle which may be substituted, or dihydrophenyl, A represents a benzene or thiophene ring which may be substituted, and X represents oxygen or a single bond, a process for preparing them and pharmaceutical compositions active against bacterial infections containing these compounds.

16 Claims, No Drawings

ACYLAMINOPENICILLANIC ACIDS AND PROCESS FOR PREPARING THEM

The present invention provides novel penicillins of the general formula I

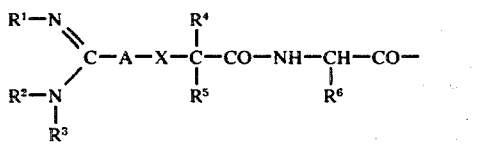

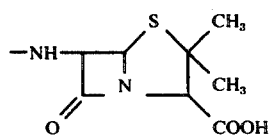

in which $R^1$, $R^2$ and $R^3$ represent hydrogen or lower alkyl which may be substituted, and in which the radicals $R^1$ and $R^2$ or $R^2$ and $R^3$ each together may form an alkylene radical which may be substituted, $R^4$ $R^5$ represent hydrogen or lower alkyl, $R^6$ represents phenyl which may be substituted, a monocyclic aromatic heterocycle which may be substituted or dihydrophenyl, A represents a benzene or thiophene ring which may be substituted, and X represents oxygen or a single bond.

Furthermore, the invention relates to a process for preparing penicillins of the general formula I, in which $R^1$ to $R^6$, A and X have the meanings given above, which comprises a. reacting aminopenicillins of the general formula II

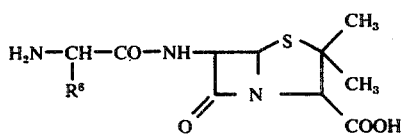

in which $R^6$ has the meaning given above, or salts or derivatives thereof which are protected at the carboxyl group, with carboxylic acids of the general formula III

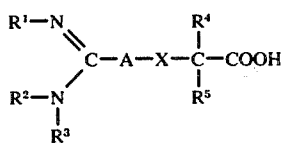

in which $R^1$ to $R^5$, A and X have the meanings given above, or with reactive derivatives of such acids, or b. reacting 6-aminopenicillanic acid or a salt or a derivative thereof which is protected at the carboxyl group, with an acid of the general formula IV

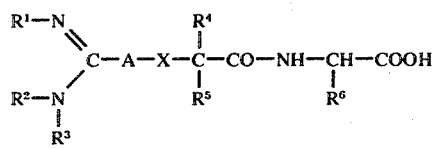

in which $R^1$ to $R^6$, A and X have the meanings given above, or with a reactive derivative of such an acid, and splitting off any protecting groups present.

If $R^1$, $R^2$ and $R^3$ represent alkyl radicals, these may be straight chain or branched alkyl radicals of 1 to 5 carbon atoms and the sum of the carbon atoms in the three radicals should not be higher than 8. Possible substituents of the alkyl radicals are, preferably, low molecular weight alkoxy groups, for example methoxy or ethoxy.

If $R^1$ and $R^2$ or $R^2$ and $R^3$ together form an alkylene radical, the latter preferably contains 2 to 4 carbon atoms. It may also be interrupted by a hetero-atom, preferably oxygen or nitrogen. As substituents of the alkylene radical, there may be used in particular low molecular alkyl radicals containing 1 to 4 carbon atoms and optionally also a hetero-atom, preferably oxygen. These alkyl radicals themselves may also be closed to a ring which may be interrupted by a hetero-atom, preferably an oxygen atom.

If $R^4$ and $R^5$ are low molecular alkyl radicals, these may contain preferably 1 to 3 carbon atoms.

$R^6$ may represent in particular phenyl, but also substituted phenyl, the substituents being, for example hydroxy, preferably in the 4-position, alkyl of 1 to 4 carbon atoms, preferably methyl, alkoxy of 1 to 4 carbon atoms, preferably methoxy, or halogen, preferably chlorine or fluorine. $R^6$ may furthermore represent dihydrophenyl such as 2,5-dihydrophenyl, or a monocyclic aromatic heterocycle, for example 2- or 3-thienyl, 2- or 3-furyl or 2- or 3-pyridyl, in which the heterocycles may also be further substituted, for example by alkyl of 1 to 4 carbon atoms, preferably methyl, or lower alkoxy, preferably methoxy.

A may represent a benzene ring or thiophene ring which may be substituted, in particular a 1,4-phenylene- or 2,5-thienylene radical. The substituents may be, for example low mlecular alkoxy of 1 to 4 carbon atoms, preferably methoxy, halogen, preferably fluorine or chlorine, or low molecular alkyl, preferably methyl.

Penicillins which fall within the scope of the invention are, for example:
6-[D,L-2-(4-amidinophenoxyacetylamino)-2-phenylacetylamino]-penicillanic acid,
6-[D-2-(4-Amidinophenoxyacetylamino)-2-P +
6-[2-(α-<4-Amidinophenoxy>-propionylamino)-2-P +
6-[2-(α-<4-Amidinophenoxy>-butyrylamino)-2-P +
6-[2-(α-<4-Amidinophenoxy>-isobutyrylamino) -2-P +
6-[2-(α-<4-Amidinophenoxy>-valerylamino)-2-P +
6-[2-(4-Amidino-2-chlorphenoxyacetylamino)-2-P +
6-[2-(4-Amidino-2-methylphenoxyacetylamino)-2-P +
6-[2-(4-Amidino-2-methoxyphenoxyacetylamino)-2-P +
6-[2-(4-Amidino-3-chlorphenoxyacetylamino)-2-P +
6-[2-(3-Amidinophenoxyacetylamino)-2-P +
6-[2-(4-Amidinophenylacetylamino)-2-P +
6-[2-(4-N-Methylamidinophenylacetylamino)-2-P +
6-[2-(4-N,N-Dimethylamidinophenylacetylamino)-2-P +
6-[2-(4-N,N'-Dimethylamidinophenylacetylamino)-2-P +
6-[2-(4-N,N,N'-Trimethylamidinophenylacetylamino)-2-P +
6-[2-(4-N-Ethylamidinophenylacetylamino)-2-P +
6-[2-(4-N,N-Diethylamidinophenylacetylamino)-2-P +
6-[2-(4-N-Propylamidinophenylacetylamino)-2-P +

6-[2-(4-N,N'-Dipropylamidinophenylacetylamino)-2-P +
6-[2-(4-N-Isopropylamidinophenylacetylamino)-2-P +
6-[2-(4-N,N'-Diisopropylamidinophenylacetylamino)-2-P +
6-[2-(4-N-Butylamidinophenylacetylamino)-2-P +
6-[2-(4-N,N-Dibutylamidinophenylacetylamino)-2-P +
6-[2-(4-N-Pentylamidinophenylacetylamino)-2-P +
6-[2-(4-N-Methyl-N-propylamidino-phenylacetylamino)-2-P +
6-[2-(4-N,N-Dimethyl-N'-ethylamidono-phenylacetylamino)-2-P +
6-[2-(2-N,N-Trimethylenamidinophenylacetylamino)-2-P +
6-[2-(4-N,N-Tetramethylenamidono-phenylacetylamino)-2-P +
6-[2-(4-N,N-Pentamethylenamidino-phenylacetylamino)-2-P +
6-[2-(4-<3-Azabicyclo[3,3,1]nonan-3-yl-carbonimidoyl>-phenylacetylamino)-2-P +
6-[2-(4-Morpholinocarbonimidoyl-phenylacetylamino)-2-P +
6-[2-(4-<4-Methylpiperazin-1-yl-carbonimidoyl>-phenylacetylamino)-2-P +
6-[2-(4-<2-Imidazolinyl>-phenylacetylamino)-2-P +
6-[2-(4-<1,5-Dimethyl-2-imidazolinyl>-phenylacetylamino)-2-P +
6-[2-(4-<1,4,5,6-Tetrahydro-2-pyrimidyl>-phenylacetylamino)-2-P +
6-[2-(4-<1-Methyl-1,4,5,6-tetrahydro-2-pyrimidyl>-phenylacetylamino)-2-P +
6-[2-(4-<1-Ethyl-1,4,5,6-tetrahydro-2-pyrimidyl>-phenylacetylamino)-2-P +
6-[2-(4-<5,5-Dimethyl-1,4,5,6-tetrahydro-2-pyrimidyl>-phenylacetylamino)-2-P +
6-[2-(4-<5,5-Diethyl-1,4,5,6-tetrahydro-2-pyrimidyl>-phenylacetylamino)-2-P +
6-[2-(4-<5,5-Dipropyl-1,4,5,6-tetrahydro-2-pyrimidyl>-phenylacetylamino)-2-P +
6-[2-(4-<5,5-Bis-methoxyethyl-1,4,5,6-tetrahydro-2-pyriminyl>-phenylacetylamino)-2-P +
6-[2-(4-N,N'-Tetramethylenamidino-phenylacetylamino)-2-P +
6-[2-(4-<1,4,6,7,8,9-Hexahydro-5H-cyclopenta[d]pyrimid-2-yl>-phenylacetylamino)-2-P +
6-[2-(4-<2,4-Diazospiro[5,5]undec-2-en-3-yl>-phenylacetylamino)-2-P +
6-[2-(4-<9-Oxa--diazospiro[5,5]undec-2-en-3-yl>-phenylacetylamino)-2-P +
6-[2-(5-Amidinothien-2-ylacetylamino)-2-P +
P + represents "phenylacetylamino]-penicillanic acid In each of the above compounds, P may also represent, for example:
2-hydroxyphenylacetylamino]-penicillanic acid
3-hydroxyphenylacetylamino]-penicillanic acid
4-hydroxyphenylacetylamino]-penicillanic acid
3,5-dihydroxyphenylacetylamino]-penicillanic acid
2-methylphenylacetylamino]-penicillanic acid
3-methylphenylacetylamino]-penicillanic acid
4-methylphenylacetylamino]-penicillanic acid
2-methoxyphenylacetylamino]-penicillanic acid
3-methoxyphenylacetylamino]-penicillanic acid
4-methoxyphenylacetylamino]-penicillanic acid
2-chlorphenylacetylamino]-penicillanic acid
3-chlorphenylacetylamino]-penicillanic acid
4-chlorphenylacetylamino]-penicillanic acid
2-fluorphenylacetylamino]-penicillanic acid
3-fluorphenylacetylamino]-penicillanic acid
4-fluorphenylacetylamino]-penicillanic acid
2,5-dihydrophenylacetylamino]-penicillanic acid
2-thienylacetylamino]-penicillanic acid
3-thienylacetylamino]-penicillanic acid
3-methyl-2-thienylacetylamino]-penicillanic acid
2-furylacetylamino]-penicillanic acid
3-furylacetylamino]-penicillanic acid
2-pyridylacetylamino]-penicillanic acid
3-pyridylacetylamino]-penicillanic acid
4-pyridylacetylamino]-penicillanic acid The acids of the general formula III may be obtained in known manner from cyano compounds of the general formula V

$$N\equiv C-A-X-\underset{\underset{R^5}{|}}{\overset{\overset{R^4}{|}}{C}}-COOR^7 \quad (V)$$

in which $R^4$, $R^5$, A and X have the meanings given above and $R^7$ represents low molecular alkyl. After conversion of the nitrile group into an imino-ether, the latter is reacted with ammonia or an amine or a diamine to the amidine and finally the carbon-ester group or an acid group resulting from it in the course of the reaction is saponified. Aminopenicillins of the formula II can be prepared, for example according to the process described in German Auslegeschrift 1 139 844.

The novel penicillins of the general formula I can be prepared by reaction of a carboxylic acid of the general formula II with an aminopenicillin of the general formula II, for example in known manner in the presence of a carbodiimide such as dicyclohexylcarbodiimide as condensation agent.

The novel penicillins of the general formula I are obtained in a particularly advantageous manner by reacting the acid of the general formula III in the form of a reactive derivative with an aminopenicillin of the general formula II. The acid chlorides have especially well proved. They may be obtained from the carboxylic acids in known manner by the action of thionyl chloride. An excess of thionyl chloride may simultaneously serve as solvent. In some cases, however, it is of advantage to carry out the reaction in the presence of an inert solvent or diluent, for example an aromatic hydrocarbon. The acid chlorides are obtained in the form of hydrochlorides which may be used directly for the further reaction. Besides the acid chlorides, also other derivatives of the carboxylic acids of th formula III may be used, for example acid bromides, activated esters, for example the p-nitrophenyl ester, the p-nitrophenylthio ester or the cyanomethyl ester, acid azides or symmetrical or mixed anhydrides.

The aminopenicillins of the general formula II are advantageously acylated in the form of their salts. Suitable salts are, for example alkali metal salts or tert. aino-salts such as the sodium, potassium or triethylamino salt. These salts may be used directly in the reaction or prepared in the reaction mixture from the aminopenicillin and suitable bases such as sodium hydrogenocarbonate, di-sodium-hydrogenophosphate or triethylamine. The acylation itself is effected in general in the presence of a solvent or diluent. Suitable for this purpose is, for example water in which the salt of the aminopenicillin of the formula II is dissolved or dispersed. It has particularly well proven to introduce the hydrochloride of the acid chloride in solid form. In order to bind the forming hydrogen chloride, another mole of a base such as sodiumhydrogenocarbonate or triethylamine is added. The reaction is carried out at room temperature or at slightly reduced temperatures, preferably between about −5° and +5° C. In general, the penicillin of the formula I precipitates in sparingly soluble form and can be isolated by filtration.

The acylation of the aminopenicillins of the formula II may also be effected in the presence of organic solvents. Solvents of the type of dimethylformamide and dimethylsulfoxide or halogenated hydrocarbons such as methylene chloride or chloroform have well provided. Dimethylformamide, in which the triethylamine salts of the aminopenicillins dissolve, is used in particularly advantageous manner. The hydrochlorides of the acid chlorides of the carboxylic acids of the formula III may be introduced in solid form into this solution, while maintaining the whole preferably at room temperature or at slightly reduced temperatures. When dimethylformamide is used as solvent, the novel penicillins that have formed generally remain dissolved. After removal of precipitated salts, they can be isolated by the addition of a suitable precipitant, for example diethyl ether or diisopropyl ether.

The reactive derivatives of the carboxylic acids of the general formula III may not be reacted with the aminopenicillins of the general formula II, but also with derivatives of these compounds. In this respect, there may be used above all the esters which may be split optionally in a neutral, acidic or weakly basic medium by solvolysis, for example by hydrolysis or alcoholysis, hydrogenolysis, by reduction, by nucleophilic exchange or photolysis, to the free carboxyl group.

Ester groups which are easily split by solvolysis with a solvent containing hydroxy groups, for example water or alcohols, preferably under neutral conditions, are those which are derived from phosphinyl-, silyl-, germanyl-, plumbyl- or stannyl-alcohols, for example those described in DOS 2 222 094 (1972), British Pat. No. 1,073,530, Netherland Patent Publication No. 67/17107 or DOS 1 800 698. Preferred are the groups of the general formula $R^7R^8P(O)$—O—CO— or $R^7R^8R^9Si$—O—CO—, in which $R^7$, $R^8$, $R^9$ may be identical or different and represent preferably lower alkyl or aryl, for example phenyl.

Esters which are easily split in an acid medium are those which are derived from lower alcohols which are polybranched in the α-position or contain one or several electron donors and optionally substituted aromatic hydrocarbons or heterocycles of aromatic nature or aroyl radicals or acyloxy radicals. As Examples thereof, there may be mentioned the tert.butyl ester, the cyclohexyl ester, the adamantyl ester, the 2-tetrahydropyranyl ester, the p-nitrobenzyl ester, the benzhydryl ester, the trityl ester, the 3,4-dimethoxybenzyl ester, the benzoylmethyl ester, the acetoxymethyl ester or the pivaloyloxymethyl ester.

Ester groups which can be split by hydrolysis in a weakly basic or acidic medium are, for example activated esters which are derived from an optionally substituted phenol or benzylalcohol, for example the 4-nitrophenyl-, 2,4-dinitrophenyl-, 4-nitrobenzyl- or triphenylmethyl ester.

The esters which are derived, for example from an optionally substituted benzyl alcohol, for example the 4-nitrobenzyl alcohol, may also be split by hydrogenolysis.

Ester groups which are derived from halogenated low molecular alcohols, for example the 2,2,2-trichloroethanol, the 2-chloroethanol, the 2-bromoethanol or the 4-pyridylmethanol, may be split reductively by treatment with nascent hydrogen or by electrolytic reduction.

Ester groups which can be split by photolysis, for example by ultraviolet light, are those derived from methanols which may be substituted by aryl. Such groups are, for example 4-methoxybenzyloxycarbonyl, 3,5-dimethoxybenzylcarbonyl or 2-nitrobenzyloxycarbonyl.

The reaction of these derivatives of the aminopenicillins of the general formula II with reactive derivatives of the carboxylic acids of the general formula III may be carried out in the presence of inert solvents or diluents in the manner indicated for the use of the salts of the formula II. It is followed by a splitting reaction, effected in known manner, for example by solvolysis, for example saponification by the action of water or diluted acids, or a reductive splitting, for example by catalytically excited hydrogen, or a photolytic splitting, for example by irradiation with ultraviolet light under neutral or acidic conditions.

The novel penicillins of the general formula I may also be obtained by reacting acids of the general formula IV with 6-aminopenicillanic acid. This can be effected, for example in known manner in the presence of a carbodiimide such as dicyclohexylcarbodiimide as condensing agent. It is particularly advantageous to use the acids of the formula IV in the form of their reactive derivatives. In this case too in particular the acid chlorides in the form of hydrochlorides have proved satisfactory. Otherwise, the reaction is carried out in a manner analogous to that described for the reaction of the acids of the general formula III with the aminopenicillins of the general formula II.

The 6-aminopenicillanic acids may also be used in the form of easily splittable derivatives. As such, there may be used in particular such esters as those already mentioned in the case of the aminopenicillins of the general formula II. If they are esters which can be easily split by hydrolysis, the reaction with the acids of the general formula IV or the derivatives thereof is carried out with the exclusion of water. Otherwise the reaction may be carried out as described for the reaction of the compounds II and III.

The acids of the general formula IV used as starting product may be obtained from the corresponding aminoacetic acids or their esters by the action of reactive derivatives of the acids of the general formula III and optional subsequent saponification of the ester groups present.

The novel penicillins of the general formula I have amphoteric character and constitute inner salts. In general, they are colourless crystalline compounds which have a different, easy solubility in water.

They have interesting antibiotic properties with a broad activity spectrum against bacterial germs. The action against gram-negative problem germs, for example Pseudomans or Proteus is particularly marked. By reason of these properties, the novel compounds represent valuable therapeutics.

The minimum inhibition concentrations of 6-[D-2-(4-<1,4,5,6-tetrahydropyrimide-2-yl>-phenylacetylamino)-2-phenylacetylamino]-pencillanic acid (compound "A", obtained according to Example 12) and Carbenicillin were determined on a series of strains. The tests were carried out according to the series dilution test with Antibiotic Medium III of Difco.

| Germs | | Minimum inhibition concentration, in weight units/ml | |
|---|---|---|---|
| | | A | Carbenicillin |
| Strept. | Aronson B | 0.125 mcg | 0.625 mcg |
| | agalactiae B | 0.195 mcg | 1.25 mcg |
| | faecium | 7.813 mcg | 62.5 mcg |
| | faecalis D | 31.25 mcg | 250.0 mcg |
| Pseud. aeruginosa | 1592E | 31.25 mcg | 125.0 mcg |
| | 1593E | 31.25 mcg | 500.0 mcg |
| | 1594E | 31.25 mcg | 250.0 mcg |

The compounds of the invention may be used as such or together with the therapeutically usual adjuvants and excipients, for example tragacanth, lactose, talc, solvents and the like, in the form of galenical preparations, for example tablets, dragees, capsules, suspensions or solutions, they may be administered perorally or, preferably, parenterally, the active substance being contained in a dosage unit, in general in a quantity of about 50 to 1000 mg, preferably about 100 to 500 mg.

For parental administration, there is preferably used a solution in water which is suitably prepared shortly before administration.

It is also possible to combine the compounds of the invention with other active substances. Thus, they may be combined and administered with other antibiotics, for example those of the series of penicillins, cephalosporins, or with compounds which have an influence on the symptomatic of bacterial infections, for example antipyretics, antiphlogistics or analgesics.

The following Examples illustrate the invention.

EXAMPLES

The novel penicillins described in the following Examples are characterized by the $R_f$-value of the thin layer chromatogram. As the layer, silica gel (Merck) and as solvent, a mixture of n-butanol-glacial acetic acid-water in a ratio of 6:2:2 were used. Development of the plates was effected by the action of iodine vapour.

EXAMPLE 1

6-[D-2-(4-Amidinophenoxyacetylamino)-2-phenylacetylamino]-penicillanic acid a. 19.4 g of 4-amidinophenoxyacetic acid and 59.5 g of thionyl chloride were well stirred for 4 hours, at a bath temperature of 65° C, in 100 ml of benzene, after addition of 2 drops of dimethylformamide. After cooling, the whole was filtered with suction, washed with benzene and diisopropyl ether and the product was dried under reduced pressure at room temperature. Yield: 23.2 g, F.p. 145° to 147° C (decomposition).

b. 5 g of 4-amidinophenoxyacetic acid chloride hydrochloride were introduced at 0° C into a solution of 7 g of anhydrous 6-(D-α-aminophenylacetylamino)-penicillanic acid and 4,46 g of triethylamine in 100 ml of anhydrous dimethylformamide. The reaction mixture was stirred for 30 minutes at 0° C and for 1 hour at room temperature. After removal of the precipitated triethylamine-hydrochloride by suction-filtration, the filtrate was slowly combined with 400 ml of diethyl ether. The powdery product which had precipitated was filtered off with suction and, in order to eliminate any triethylamino hydrochloride and 6-(D-α-aminophenylacetylamino)-penicillanic acid still present, it was distributed in a mixture of 500 ml of methylene chloride and 5 ml of triethylamine and stirred for 45 minutes. The product was filtered off with suction and washed with methylene chloride and diethyl ether. Yield: 7.55 g; decomposition point 198°–200° C. $R_f$-value = 0.52.

EXAMPLE 2

6-[D-2-(4-amidinophenoxyacetylamino)-2-phenylacetylamino]-penicillanic acid 8.06 of 6-(D-α-aminophenylacetylamino)-penicillanic acid-trihydrate and 10,08 g of sodium bicarbonate were dispersed in 100 ml of water at 0° C. 5.0 g of 4-amidinophenoxyacetic acid chloride hydrochloride were introduced, while well stirring, and the whole was stirred for 30 minutes at 0° C. The product was then filtered off with suction, washed with ice water and dried under reduced pressure. 7.8 g of a raw product were obtained which were then treated as described in Example 1(b) with methylene chloride and triethylamine. 6.6 g of colourless crystals were obtained. In order to eliminate small amounts of 4-amidinophenoxy-acetic acid, the product was treated with 100 ml of dimethylformamide and undissolved matter was filtered off with suction. From the filtrate, the 6-[D2-(4-amidinophenoxyacetylamino)-2-phenylacetylamino]-penicillanic acid was precipitated by the addition of diethyl ether. Yield: 2 g; decomposition point 198° to 200° C; $R_f$-value = 0.52.

EXAMPLE 3

6-[D-2-(4-amidinophenoxyacetylamino)-2-(4-hydroxyphenyl)-acetylamino]-penicillanic acid 4.5 g of anhydrous 6-(D-α-amino-4-hydroxyphenylacetylamino)-penicillanic acid and 2.52 g of triethylamine were dissolved at 0° C in 60 ml of anhydrous dimethylformamide and, at the same temperature, 3.05 g of 4-amidinophenoxyacetic acid chloride hydrochloride were introduced. The reaction mixture was then stirred for 90 minutes at 0° C and the triethylaminehydrochloride was filtered off with suction. Upon addition of diethyl ether, the above-mentioned penicillin precipitated from the filtrate. This raw product was treated as described in Example 1(b) with methylene chloride and triethylamine. After suction-filtration, washing with methylene chloride and diethyl ether and drying under pressure reduced pressure, the yield was 4.7 g. Decomposition point 192° to 194° C; $R_f$-value = 0.50.

EXAMPLE 4

6-[D-2-(3-amidinophenoxyacetylamino)-2-phenylacetylamino]-penicillanic acid a. 19.4 g of 3-amidinophenoxyacetic acid were heated under reflux, while well stirring, for 2 hours with 70 ml of thionyl chloride. After cooling, filtration with suction and washing with anhydrous diethyl ether, 21 g of 3-amidinophenoxyacetic acid chloride hydrochloride were obtained; decomposition point 149° to 151° C.

b. 7 g of anhydrous 6-(D-α-aminophenylacetylamino)-penicillanic acid and 4.46 g of triethylamine were dissolved at 0° C in 100 ml of anhydrous dimethylformamide and then, 5.0 g of 3-amidinophenoxyacetic acid chloride-hydrochloride were added portionwise. The reaction mixture was stirred for 30 minutes at 0° C and for 1 hour at room temperature. Working up was effected as described in Example 1(b). Yield: 5.6 g; decomposition point 196° to 198° C; $R_f$ value = 0.53.

EXAMPLE 5

6-[D-2-(4-amidinophenylacetylamino)-2-phenylacetylamino]-penicillanic acid a. The 4-amidinophenylacetic acid chloride-hydrochloride was obtained from 4-amidinophenylacetic acid was described in Example 1(a). Decomposition point: 174° to 177° C.

b. Starting from 8.75 g of 6-(D-α-aminophenylacetylamino)-penicillanic acid (anhydrous) and 5.82 g of 4-amidino phenylacetic acid chloride-hydrochloride, there were obtained in a manner analogous to the method described in Example 1(b), 10.5 g of the above-mentioned compound. Decomposition point: 190° to 193° C; $R_f$-value = 0.46.

EXAMPLE 6

6-[D-2-(4-amidino-2-methoxyphenoxyacetylamino)-2-phenylacetylamino]-penicillanic acid a. According to the method described in Example 1(a), there was prepared the 4-amidino-2-methoxyphenoxyacetic acid chloride-hydrochloride from 6.8 g of 4-amidino-2-methoxy-phenoxyacetic acid and a mixture of 30 ml of benzene and 30 ml of thionyl chloride. Decomposition point: 153° to 156° C.

b. By the reaction of 8.75 g of 6-(D-α-aminophenylacetylamino)-penicillanic acid (anhydrous) with 7 g of 4-amidino-2-methoxyphenoxyacetic acid chloride-hydrochloride according to the method described in Example 1(b), there were obtained 11 g of the above-mentioned penicillin. Decomposition point 189° to 191° C; $R_f$-value = 0.45.

EXAMPLE 7

6-[D-2-(4-amidinophenoxyisobutyrylamino)-2-phenylacetylamino]-penicillanic acid a. 25 ml of thionyl chloride was poured over 4.44 g of 4-amidinophenoxyisobutyric acid and the whole was stirred for 2 hours at room temperature. After some minutes, a clear solution was obtained. Then, 100 ml of anhydrous diethyl ether were introduced, while stirring and the crystallizing 4-amidinophenoxyisobutyric acid chloride-hydrochloride was filtered off with suction and washed with anhydrous ether. Yield: 5 g; decomposition point 160° to 161° C.

b. By working as described in Example 1(b), there were obtained from 6.3 g of anhydrous 6-(D-α-aminophenylacetylamino)-penicillanic acid and 5.0 g of 4-amidino-phenoxyisobutyric acid chloride-hydrochloride, 7.2 g of the above-mentioned penicillin. Decomposition point: 191°; $R_f$-value = 0.57.

EXAMPLE 8

6-[D-2-(4-<-imidazolinyl>-phenoxyacetylamino)-2-phenylacetylamino]-penicillanic acid a. 5.8 g of 4-(2-imidazolinyl)-phenoxyacetic acid were heated for 4 hours under reflux with 40 ml of benzene and 40 ml of thionyl chloride and stirred. The reaction mixture was then cooled and the 4-(2-imidazolinyl)-phenoxyacetic acid chloride-hydrochloride that had crystallized was filtered off with suction and washed with anhydrous ether. Yield: 6.4 g; decomposition point from 195° C onwards.

b. Under the conditions described in Example 1(b), there were obtained from 7.0 g of anhydrous 6-(D-α-aminophenylacetylamino)-penicillanic acid and 5.5 g of 4-(2-imidazolinyl)-phenoxyacetic acid chloride-hydrochloride, 6.5 g of the above-mentioned penicillin. Decomposition point: 200° to 202° C; $R_f$-value = 0.35.

EXAMPLE 9

6-[D-2-(4-<1,4,5,6-tetrahydropyrimide-2-yl>-phenoxyacetylamino)-2-phenylacetylamino]-penicillanic acid a. 5.4 g of 4-(1,4,5,6-tetrahydropyrimide-2-yl)-phenoxyacetic acid hydrochloride were combined with 40 ml of thionyl chloride and the whole was heated for 1 hour under reflux. After cooling, the reaction solution was combined slowly with 100 ml of anhydrous diethyl ether. Thereupon, the 4-(1,4,5,6-tetrahydropyrimide-2-yl)-phenoxyacetic acid chloride-hydrochloride crystallized; it was filtered off with suction and washed with anhydrous ether. Yield: 5.6 g; decomposition point 200° to 202° C.

b. The above-mentioned penicillin was obtained in a manner analogous to that described in Example 1(b) from 6.55 g of anhydrous 6-(D-α-aminophenylacetylamino)-penicillanic acid and 5.4 g of 4-(1,4,5,6-tetrahydropyrimide-2-yl)-phenoxyacetic acid chloride-hydrochloride. Yield: 8.4 g; decomposition point: 211° to 213° C; $R_f$-value = 0.37.

EXAMPLE 10

6-[D-2-(4-<5,5-dimethyl-1,4,5,6-tetrahydropyrimide-2-yl>-phenoxy-acetylamino)-2-phenylacetylamino]-penicillanic acid a. A mixture of 5.24 of 4-(5,5-dimethyl-1,4,5,6-tetrahydropyrimide-2-yl)-phenoxyacetic acid and 20 ml of thionyl chloride was stirred for 1 hour at 40° C. The reaction mixture was then poured into 100 ml of anhydrous diethyl ether and the 4-(5,5-dimethyl-1,4,5,6-tetrahydropyrimide-2-yl)-phenoxyacetic acid chloride-hydrochloride that had precipitated was filtered off with suction, washed with ether and dried under reduced pressure. Yield: 5.8 g; decomposition point 185° C.

b. In a manner analogous to that described in Example 1(b), there were obtained from 6.3 g of anhydrous 6-(D-α-aminophenylacetylamino)-penicillanic acid and 5.8 g of 4-(5,5-dimethyl-1,4,5,6-tetrahydropyrimide-2-yl)-phenoxyacetic acid chloride-hydrochloride, 5.8 g of the above-mentioned compound. Decomposition point 195° C. $R_f$-value = 0.51.

EXAMPLE 11

6-[D-2-(4-<9-oxa-2,4-diazaspiro[5,5]undec-2-ene-3-yl>-phenoxy-acetylamino)-2-phenylacetylamino]-penicillanic acid a. 3.4 g of 4-(9-oxa-2,4-diazaspiro[5,5]undec-2-ene-3-yl)-phenoxyacetic acid hydrochloride and 15 ml of thionyl chloride were heated for about 20 minutes on the steam bath until dissolution was complete. The whole was allowed to stand for several hours at room temperature, poured into 100 ml of anhydrous diethyl ether and the 6-(9-oxa-2,4-diazaspiro[5,5]undec- 2-ene-3-yl)-phenoxyacetic acid chloride-hydrochloride that had precipitated in crystalline form was filtered off with suction. Yield: 2.5 g; decomposition point from 198° C onwards.

b. 2.45 g of anhydrous 6-(D-α-aminophenylacetylamino)-penicillanic acid were reacted in a manner analogous to that described in Example 1(b) with 2.5 g of 4-(9-oxa-2,4-diazaspiro[5,5]undec-2-ene-3-yl)-phenoxyacetic acid chloride-hydrochloride, whereupon 3.5 g of the above mentioned penicillin were obtained. Decomposition point: 210° to 212° C; $R_f$-value = 0.41.

EXAMPLE 12

6-[D-2-(4-<1,4,5,6-Tetrahydropyrimide-2-yl>-phenylacetylamino]-2-phenylacetylamino]-penicillanic acid a. 5.08 g of 4-(1,4,5,6-tetrahydropyrimide-2-yl)-phenylacetic acid hydrochloride were reacted with 15 ml of thionyl chloride in a manner analogous to that described in Example 7(a), whereupon 5.3 g of 4-(1,4,5,6-tetrahydropyrimide-2-yl)-phenylacetic acid chloride-hydrochloride were obtained.

b. 3.5 g of anhydrous 6-(D-α-aminophenylacetylamino)-penicillanic acid were reacted with 2.73 g of 4-(1,4,5,6-tetrahydropyrimide-2-yl)-phenylacetic acid chloride-hydrochloride in a manner analogous to that described in Example 1(b), whereby 3.95 g of the above-mentioned compound were obtained. For further purification, the substance was dissolved in water, filtered and lyophilized. $R_f$-value = 0.41.

EXAMPLE 13

6-[D-2-(4-<N,N-Pentamethyleneamidino>-phenoxyacetylamino)-2-phenylacetylamino]-penicillanic acid a. 5.97 g of 4-(N,N-pentamethyleneamidino)-phenoxyacetic acid-hydrochloride were reacted with mixture of 25 ml of benzene and 25 ml of thionyl chloride in a manner analogous to that described in Example 8(a). 6.0 g of 4-(N,N-Pentamethyleneamidino)-phenoxyacetic acid chloride-hydrochloride were obtained; decomposition point 186° to 188° C.

b. 6.5 g of anhydrous 6-(D-α-aminophenylacetylamino)-penicillanic acid and 5.9 g of 4-(N,N-pentamethyleneamidino)-phenoxyacetic acid chloride-hydrochloride were reacted as described in Example 1(b). Yield: 5.0 g of the above-specified penicillin; $R_f$-value = 0.46.

EXAMPLE 14

6-[D-2-(4-<3-Azabicyclo[3.3,1]nonane-3-yl-carbonimidoyl>-phenyoxyacetylamino)-2-phenylacetylamino]-penicillanic acid a. 6.04 g of 4-(3-azabicyclo[3,3,1]nonane-3-ylcarbonimdoyl)-phenoxyacetic acid were reacted as described in Example 8(a) with a mixture of 25 ml of benzene and 25 ml of thionyl chloride. Yield: 7.0 g of 4-(3-azabicyclo[3,3,1]nonane-3-ylcarbonimidoyl)-phenoxyacetic acid chloride-hydrochloride.

b. 6.84 g of 6-(D-α-amino-phenylacetylamino)-penicillanic acid (anhydrous) were reacted in a manner analogous to the method described in Example 1(b) with 7.0 g of 4-(3-azabicyclo-[3,3,1]nonane-3-ylcarbonimidoyl-phenoxyacetic acid chloride-hydrochloride. For further purification, the crude product obtained was treated with 30 ml of water, filtered off with suction, washed well with water and dried under reduced pressure. Yield: 8.0 g; decomposition point about 190° C; $R_f$-value = 0.51.

EXAMPLE 15

6-[D-2-(4-<2-Imidazolinyl>-phenylacetylamino)-2-phenylacetyl-amino]-penicillanic acid a. 10 g of 4-(2-Imidazolinyl)-phenylacetic acid were stirred for 5 hours at 55° C with a mixture of 150 ml of benzene and 90 ml of thionyl chloride. The reaction mixture was then cooled, filtered with suction, washed with benzene and diethyl ether and dried under reduced pressure. 11 g of 4-(2-Imidazolinyl)-phenylacetic acid chloride-hydrochloride were obtained.

b. 4.05 g of anhydrous 6-(D-α-aminophenylacetylamino)-penicillanic acid and 3.0 g of 4-(2-imidazolinyl)-phenylacetic acid chloride-hydrochloride were reacted in a manner analogous to that described in Example 1(b). 3.6 g of the above-specified penicillin were obtained. For further purification, the product was dissolved in 100 ml of water, filtered and lyophilized. $R_f$-value = 0.38.

EXAMPLE 16

6-[D-2-(4-<2,4-Diazospiro[5,5]undec-2-ene-3-yl>-phenylacetylamino)-2-phenylacetylamino]-penicillanic acid a. 4.27 g of 4-(2,4-diazospiro[5,5]undec-2-ene-3-yl)-phenylacetic acid hydrochloride were reacted with 10 ml of thionyl chloride in a manner analogous to that described in Example 7(a). 4.08 g of 4-(2,4-diazospiro-[5,5]undec-2-ene-3-yl)-phenylacetic acid chloride-hydrochloride were obtained in the form of colourless crystals.

b. 4.1 g of anhydrous 6-(D-α-aminophenylacetylamino)-penicillanic acid and 4.0 g of 4-(2.4-diazospiro[5,5]undec-2-3n-3-yl)-phenylacetic acid chloride-hydrochloride were reacted under the same conditions as described in Example 1(b). 5.6 g of the above-mentioned penicillin were obtained; decomposition point 212° to 214° C; $R_f$-value = 0.56.

EXAMPLE 17

6-[D-2-(4-<9-Oxa-2,4-diazospiro-[5,5]undec-2-2n-3-3-yl>-phenylacetylamino)-2-phenylacetylamino]-penicillanic acid a. 3.25 g of 4-(9-oxa-2,4-diazospiro[5,5]undec-2-ene-3-yl)-phenylacetic acid hydrochloride were reacted with 10 ml of thionyl chloride in a manner analogous to that described in Example 7(a). 3.4 g of 4-(9-oxa-2,4-diazospiro[5,5]undec-2-ene-3-yl)-phenylacetic acid chloride-hydrochloride in the form of colourless crystals were obtained. Decomposition point 235° to 238° C.

b. 3.36 of anhydrous 6-(D-α-aminophenylacetylamino)-penicillanic acid were reacted with 3.3 g of 4-(9-oxa-2,4-diazospiro-[5,5]undec-2-ene-3-yl)-phenylacetic acid chloride-hydrochloride according to the method described in Example 1(b). 3.8 g of the above-specified penicillin were obtained. $R_f$-value = 0.36.

EXAMPLE 18

6-[D-2-(5-Amidino-2-thienylacetylamino)-2-phenylacetylamino]-penicillanic acid a. 7.36 g of 5-amidino-2-2-thienylacetic acid were stirred for 2 hours at room temperature with a mixture of 60 ml of anhydrous benzene and 15 ml of thionyl chloride. The 5-amidino-2-thienylacetic acid chloride-hydrochloride was filtered off with suction and washed with benzene and diethyl ether. After drying under reduced pressure, 9.0 g of the above-specified acid chloride-hydrochloride were obtained; decomposition point 158° to 160° C.

b. 12.35 g of anhydrous 6-(D-α-amino-phenylacetylamino)-penicillanic acid and 8.36 g of 5-amidino-2-thienylacetic acid chloride-hydrochloride were reacted in a manner analogous to that described in Example 1(b). 10.7 g of the above-specified penicillin were obtained; decomposition point 199° to 200° C. $R_f$-value = 0.61.

EXAMPLE 19

6-[D-2-(4-amidinophenoxyacetylamino)-2-phenylacetylamino]-penicillanic acid 2.2 g of trimethyl-chlorosilane were added dropwise, at 0° C, to a solution of 3.5 g of anhydrous 6-(D-α-amino-phenylacetylamino)-penicillanic acid and 2.02 g of triethylamine in 60 ml of anhydrous methylene chloride. The reaction solution was stirred for 1 hour at 0° C and then combined at first with 2.02 g of triethylamine and subsequently with 2.5 g of 4-amidino-phenoxyacetic acid chloride-hydrochloride. The reaction mixture was stirred for 1 hour at 0° C and for another hour at room temperature. After removal of the methylene chloride by distillation, the residue was triturated with 25 ml of water. The product that precipitated in the form of a powder was filtered off with suction, washed with water and dried under reduced pressure. In order to eliminate any triethylamine-hydrochloride and 6-(D-α-amino-phenylacetylamino)-penicillanic acid still present, the compound was treated in the same manner as described in Example 1(b) with a mixture of methylene chloride and triethylamine. 3.4 g of the above-specified penicillin were obtained. Decomposition point 198° to 200° C; $R_f$-value = 0.53.

We claim:

1. Acylaminopenicillanic acids of the general formula I

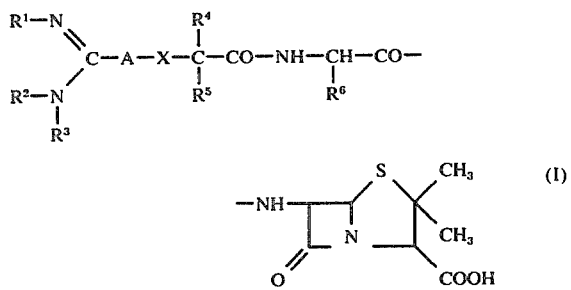

in which $R^1$, $R^2$ and $R^3$ represent hydrogen or lower alkyl radicals which may be substituted by lower alkoxy and in which the radicals $R^1$ and $R^2$ or $R^2$ and $R^3$ may form together an alkylene radical of 2 to 4 carbon atoms which may be interrupted by oxygen or nitrogen and which may be substituted by lower alkyl radicals which may be interrupted by oxygen and wherein these substituents of the alkylene ring may further be closed to form a ring which may be interrupted by oxygen;

$R^4$ and $R^5$ represent hydrogen or lower alkyl, $R^6$ represents phenyl which may be substituted by hydroxyl, lower alkyl, lower alkoxy or halogen; dihydrophenyl; or thienyl, furyl or pyridyl which may be substituted by lower alkyl or lower alkoxy;

A represents a benzene or thiophene ring which may be substituted by lower alkoxy, haogen or lower alkyl, and X represents oxygen or a single bond.

2. 6-[D,L-2-(4-Amidinophenoxyacetylamino)-2-phenylacetylamino]-penicillanic acid.

3. 6-[D-2-(4-Amidinophenoxyacetylamino)-2-phenylacetylamino]-penicillanic acid.

4. 6-[D-2-(4-Amidinophenoxyacetylamino)-2-(4-hydroxyphenyl)-acetylamino]-penicillanic acid.

5. 6-[D-2-(3-Amidinophenoxyacetylamino)-2-phenylacetylamino]-penicillanic acid.

6. 6-[D-2-(4-Amidinophenylacetylamino)-2-phenylacetylamino]-penicillanic acid.

7. 6-[D-2-(4-Amidino-2-methoxyphenoxyacetylamino)-2-phenylacetylamino]-penicillanic acid.

8. 6-[D-2-(4-Amidinophenoxyisobutyrylamino)-2-(phenylacetylamino]-penicillanic acid.

9. 6-[D-2-(4-<2-Imidazolinyl>-phenoxyacetylamino)-2-phenylacetylamino]-penicillanic acid.

10. 6-[D-2-(4-<1,4,5,6-Tetrahydropyrimide-2-yl>-phenoxyacetylamino)-2-phenylacetylamino]-penicillanic acid.

11. 6-[D-2-(4-<5,5-Dimethyl-1,4,5,6-tetrahydropyrimide-2-yl>-phenoxyacetylamino)-2-phenylacetylamino]-penicillanic acid.

12. 6-[D-2-(4-<9-Oxa-2,4-diazaspiro[5,5]undec-2-ene-3-yl>-phenoxyacetylamino)-2-phenylacetylamino]-penicillanic acid.

13. 6-[D-2-(4-<1,4,5,6-Tetrahydropyrimide-2-yl>-phenylacetylamino)-2-phenylacetylamino]-penicillanic acid.

14. 6-[D-2-(4-<N,N-Pentamethyleneamidino>-phenoxyacetylamino)-2-phenylacetylamino]-penicillanic acid.

15. 6-[D-2-(4-<3-Azabicyclo[3,3,1]nonane-3-yclcarbonimidoyl>-phenoxyacetylamino)-2-phenylacetylamino]-penicillanic acid.

16. A pharmaceutical composition active against bacterial infections and comprising a pharmaceutically acceptable carrier and an antibacterially effective amount of an acylaminopenicillanic acid of the general formula I

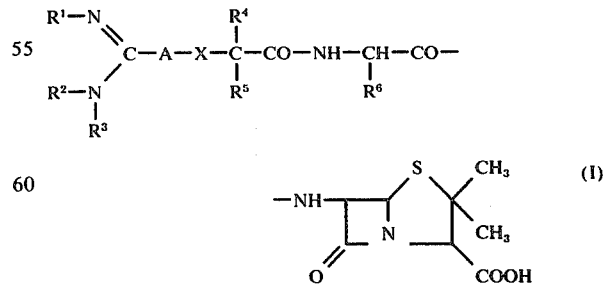

in which $R^1$ to $R^6$, A and X have the meanings given above in claim 1.

* * * * *